United States Patent
Di Carlo et al.

(10) Patent No.: US 10,502,674 B2
(45) Date of Patent: *Dec. 10, 2019

(54) APPARATUS AND METHOD FOR LABEL-FREE ANALYSIS OF RARE CELLS FROM BODILY FLUIDS

(71) Applicant: THE REGENTS OF THE UNIVERSITY OF CALIFORNIA, Oakland, CA (US)

(72) Inventors: Dino Di Carlo, Los Angeles, CA (US); Derek Go, Walnut, CA (US); Mahdokht Masaeli, Los Angeles, CA (US); Elodie Sollier, Gagny (FR)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 22 days.

This patent is subject to a terminal disclaimer.

(21) Appl. No.: 15/320,286

(22) PCT Filed: Jun. 26, 2015

(86) PCT No.: PCT/US2015/038117
§ 371 (c)(1),
(2) Date: Dec. 19, 2016

(87) PCT Pub. No.: WO2015/200857
PCT Pub. Date: Dec. 30, 2015

(65) Prior Publication Data
US 2017/0248512 A1 Aug. 31, 2017

Related U.S. Application Data
(60) Provisional application No. 62/018,415, filed on Jun. 27, 2014.

(51) Int. Cl.
*G06K 9/00* (2006.01)
*G01N 15/14* (2006.01)
(Continued)

(52) U.S. Cl.
CPC ......... *G01N 15/1475* (2013.01); *C12M 47/04* (2013.01); *G01N 15/0227* (2013.01);
(Continued)

(58) Field of Classification Search
CPC ........... G01N 15/0612; G01N 15/0618; G01N 15/0656; G01N 15/1456; G01N 15/1484;
(Continued)

(56) References Cited

U.S. PATENT DOCUMENTS 7,803,599 B2 9/2010 Lutz et al.
9,005,455 B2 4/2015 Achard et al.
(Continued)

FOREIGN PATENT DOCUMENTS

WO WO 02/092222 11/2002
WO WO 2008/157257 12/2008
(Continued)

OTHER PUBLICATIONS

PCT International Preliminary Report on Patentability (Chapter I of the Patent Cooperation Treaty) for PCT/US2015/038117, Applicant: The Regents of the University of California, Form PCT/IB/326 and 373, dated Jan. 5, 2017 (8pages).
(Continued)

*Primary Examiner* — Solomon G Bezuayehu
(74) *Attorney, Agent, or Firm* — Vista IP Law Group LLP

(57) ABSTRACT

A system and method for the label-free analysis of cells includes a purification device configured to receive a heterogeneous population of cells, the purification device temporarily trapping therein a subpopulation of cells from the heterogeneous population of cells and a cell analysis device
(Continued)

positioned downstream of the purification device and configured to measure one or more cellular parameters including cell count, measured cell size, and/or cell morphology. In an alternative embodiment, the subpopulation of cells is analyzed while they are trapped within the purification device.

17 Claims, 10 Drawing Sheets

(51) Int. Cl.

| | |
|---|---|
| G01N 15/02 | (2006.01) |
| G01N 15/12 | (2006.01) |
| C12M 1/00 | (2006.01) |
| G01N 33/50 | (2006.01) |
| G01N 33/49 | (2006.01) |
| G01N 33/493 | (2006.01) |
| G06T 7/00 | (2017.01) |
| G01N 15/10 | (2006.01) |

(52) U.S. Cl.
CPC ......... *G01N 15/12* (2013.01); *G01N 15/1404* (2013.01); *G01N 15/1429* (2013.01); *G01N 15/1459* (2013.01); *G01N 15/1463* (2013.01); *G01N 15/1484* (2013.01); *G01N 33/49* (2013.01); *G01N 33/493* (2013.01); *G01N 33/5005* (2013.01); *G06T 7/0012* (2013.01); *G01N 2015/0294* (2013.01); *G01N 2015/1006* (2013.01); *G01N 2015/1263* (2013.01); *G01N 2015/1486* (2013.01); *G01N 2015/1493* (2013.01); *G01N 2015/1497* (2013.01)

(58) Field of Classification Search
CPC ... G01N 2015/0681; G01N 2015/0693; G01N 2015/1006; G01N 2015/149; G01N 2035/00237; G01N 2035/00356; G01N 2035/1034
USPC .......................... 382/128–134; 435/7.1, 177
See application file for complete search history.

(56) References Cited

U.S. PATENT DOCUMENTS

| | | | |
|---|---|---|---|
| 9,133,499 | B2 | 9/2015 | Di Carlo et al. |
| 2005/0048581 | A1 | 3/2005 | Chiu et al. |
| 2007/0099207 | A1* | 5/2007 | Fuchs ............... B01L 3/502753 |
| | | | 435/6.16 |
| 2007/0190525 | A1 | 8/2007 | Gu et al. |
| 2008/0009780 | A1 | 1/2008 | Leonard et al. |
| 2008/0318324 | A1 | 12/2008 | Chiu et al. |
| 2009/0014360 | A1 | 1/2009 | Toner et al. |
| 2009/0286300 | A1 | 11/2009 | Le Vot et al. |
| 2010/0247492 | A1 | 9/2010 | Kuhn et al. |
| 2010/0279321 | A1 | 11/2010 | Chin et al. |
| 2011/0070581 | A1 | 3/2011 | Gupta et al. |
| 2011/0096327 | A1 | 4/2011 | Papautsky et al. |
| 2011/0117577 | A1 | 5/2011 | Reboud et al. |
| 2013/0052664 | A1* | 2/2013 | Park ...................... G01N 33/543 |
| | | | 435/7.23 |
| 2013/0130226 | A1* | 5/2013 | Lim .................... B01L 3/50273 |
| | | | 435/2 |
| 2013/0171628 | A1* | 7/2013 | Di Carlo ........... B01L 3/502746 |
| | | | 435/6.1 |
| 2013/0295580 | A1* | 11/2013 | McDevitt ......... G01N 33/57407 |
| | | | 435/6.14 |
| 2013/0314526 | A1* | 11/2013 | Yasuda .............. G01N 15/1475 |
| | | | 348/79 |
| 2015/0132766 | A1* | 5/2015 | Yasuda .............. G01N 21/6458 |
| | | | 435/7.1 |
| 2015/0174549 | A1* | 6/2015 | Lim ....................... C01G 49/02 |
| | | | 514/5.9 |
| 2015/0238963 | A1* | 8/2015 | Han .................. B01L 3/502753 |
| | | | 435/30 |
| 2015/0355060 | A1 | 12/2015 | Di Carlo et al. |
| 2016/0139015 | A1 | 5/2016 | Di Carlo et al. |
| 2016/0146823 | A1* | 5/2016 | Chiu .................. G01N 21/6428 |
| | | | 506/9 |

FOREIGN PATENT DOCUMENTS

| | | |
|---|---|---|
| WO | WO 2010/036912 | 4/2010 |
| WO | WO 2013/156081 | 10/2013 |

OTHER PUBLICATIONS

Bhagat, Ali Asgar S. et al., Pinched flow coupled shear-modulated inertial microfluidics for high-throughput rare blood cell separation, Lab Chip, 2011, 11, 1870-1878.
Cristofanilli, Massimo et al., Circulating Tumor Cells: A Novel Prognostic Factor for Newly Diagnosed Metastatic Breast Cancer, J. Clinic Onc., 23, 7, Mar. 1, 2005, 1420-1430.
Lin, Cheng Ming et al., Trapping of Bioparticles via Microvortices in a Microfluidic Device for Bioassay Applications, Anal. Chem. 2008, 80, 8937-8945.
Nagrath, Sunitha et al., Isolation of rare circulating tumour cells in cancer patients by microchip technology, Nature, 450, 1235-1239 (Dec. 20, 2007).
Moon, Hui-Sung et al., Continuous separation of breast cancer cells from blood samples using multi-orifice flow fractionation (MOFF) and dielectrophoresis (DEP), Lab Chip, 2011, 11, 1118-1125.
Park, Jae-Sung et al., Continuous focusing of microparticles using inertial lift force and vorticity via multi-orifice microfluidic channels, Lab Chip, 2009, 9, 939-948.
Stott, Shannon L. et al., Isolation of circulating tumor cells using a microvortex-generating herringbone-chip, PNAS, Oct. 26, 2010, vol. 107, No. 43, 18392-18397.
Sethu, Palaniappan et al., Microfluidic Isolation of Leukocytes from Whole Blood for Phenotype and Gene Expression Analysis, Anal. Chem., 2006, 78, 5453-5461.
Hur, Soojung Claire et al., High-throughput size-based rare cell enrichment using microscale vortices, Biomicrofluidics, vol. 5(2), pp. 22206-01-22206-10 (Jun. 29, 2011).
Mach Albert J. et al., Continuous Scalable Blood Filtration Device Using Inertial Microfluidics, Biotechnology and Bioengineering, vol. 107, No. 2, Cotber 1, 2010, pp. 301-311.
Park, Jae-Sung et al., Multiorifice Flow Fractionation: Continuous Size-Based Separation of Microspheres Using a Series of Contraction/Expansion Microchannels, Anal. Chem. 2009, 81, pp. 8280-8288.
PCT International Search Report for PCT/US2011/051224, Applicant: The Regents of the University of California, Form PCT/ISA/210 and 220, dated Apr. 18, 2012 (4pages).
PCT Written Opinion of the International Search Authority for PCT/US2011/051224, Applicant: The Regents of the University of California, Form PCT/ISA/237, dated Apr. 18, 2012 (4pages).
PCT International Preliminary Report on Patentability (Chapter I of the Patent Cooperation Treaty) for PCT/US2011/051224, Applicant: The Regents of the University of California, Form PCT/IB/326 and 373, dated Mar. 28, 2013 (6pages).
Patent Examination Report No. 1, dated Jul. 15, 2014, in Australian Patent Application No. 2011302302, Application: The Regents of the University of California (10pages).
Chiu, D.T., Cellular manipulations in microvortices, Anal Bioanal Chem (2007) 387:17-20.
Khabiry, M. et al., Cell Docking in Double Grooves in a Microfluidic Channel, NIH Public Access Author Manuscript, 2009, [Retrieved on Feb. 13, 2014]. Retrieved from the Internet <URL:http://www.ncbi.nih.gov/pmc/articles/PMC2683980/> published in final edited form as: Small, 5(10):1186-1194.
Lee, M.G. et al., Three-dimensional hydrodynamic focusing with a single sheath flow in a single-layer microfluidic device, Lab on a Chip, 2009, 9(21):3155-3160.

(56) References Cited

OTHER PUBLICATIONS

Lettieri, G.L, et al., A novel microfluidic concept for bioanalysis using freely moving beads trapped in recirculating flows, Lab on a Chip, 2003, 3(1):34-39.
Shelby, J.P., et al, High radial acceleration in microvortices, Nature, 2003, 425:38.
Notification of the First Office Action including an English translations prepared by Kangxin Partners, P.C.dated Feb. 17, 2014, in Chinese Patent Application No. 201180044092.8 Application: The Regents of the University of California (16pages).
Notification of the Second Office Action including an English translations prepared by Kangxin Partners, P.C. dated Aug. 5, 2014, in Chinese Patent Application No. 201180044092.8 Application: The Regents of the University of California (8pages).
Notice of Acceptance dated Nov. 26, 2014 in Australian Patent Application No. 2011302302, Applicant: The Regents of the University of California (3pages).
Karino et al., 1977. Flow Behaviour of Blood Cells and Rigid Spheres in an Annular Vortex. Philosophical Transactions of the Royal Society of London. Series B, Biological Sciences, vol. 279, No. 967, pp. 413-445.
Gossett et al. 2010. Label-free cell separation and sorting in microfluidic systems. Analytical and Bioanalytical Chemistry, vol. 397, pp. 3249-3267.
Bergman et al. 1995-2006. Anatomy Atlases, A digital library of anatomy information, 9 pages.
Hsu et al. 2008. Microvortex for focusing, guiding and sorting of particles. Lab on a Chip, vol. 8, pp. 2128-2134.
Sollier, Elodie et al., Passive microfluidic devices for plasma extraction from whole human blood, Sens. Actuators B: Chem. (2009), doi:10.1016/j.snb.2009.05.023.
Sollier, Elodie et al., Fast and continuous plasma extraction from the whole human blood based on expanding cell-free layer devices, Biomed Microdevices (2010) 12:485-497.
PCT International Search Report for PCT/US2015/038117, Applicant: The Regents of the University of California, Form PCT/ISA/210 and 220, dated Sep. 18, 2015 (8pages).
PCT Written Opinion of the International Search Authority for PCT/US2015/038117, Applicant: The Regents of the University of California, Form PCT/ISA/237, dated Sep. 18, 2015 (6pages).
Adams, Andre A. et al., Highly Efficient Circulating Tumor Cell Isolation from Whole Blood and Label-Free Enumeration Using Polymer-Based Microfluidics with an Integrated Conductivity Senor, J. Am. Chem. Soc. 2008, 130, 8633-8641.
Yang, Sung-Yi et al., A cell counting/sorting system incorporated with a microfabricted flow cytometer chip, Meas. Sci. Technol. 17 (2006) 2001-2009.
Notice of Rejection dated Sep. 29, 2015 in Japanese Patent Application No. 2013-528369, Applicant: The Regents of the University of California, (3pges).
First Office Action dated Jan. 19, 2016 in Chinese Patent Application No. 2015100887109, Applicant: The Regents of the University of California, (16pgs).
Extended European Search Report (EESR) dated Apr. 4, 2016 in European Patent Application No. 11825738.5, Applicant: The Regents of the University of California, (7pgs).
Patent Examination Report No. 1 dated Jan. 15, 2016 in Australian Patent Application No. 2015200910, Applicant: The Regents of the University of California, (5pgs).
Patent Examination Report No. 2 dated Apr. 4, 2016 in Australian Patent Application No. 2015200910, Applicant: The Regents of the University of California, (3pgs).
Notice of Acceptance dated Sep. 7, 2016 in Australian Patent Application No. 2015200910, Applicant: The Regents of the University of California, (1pg).

* cited by examiner

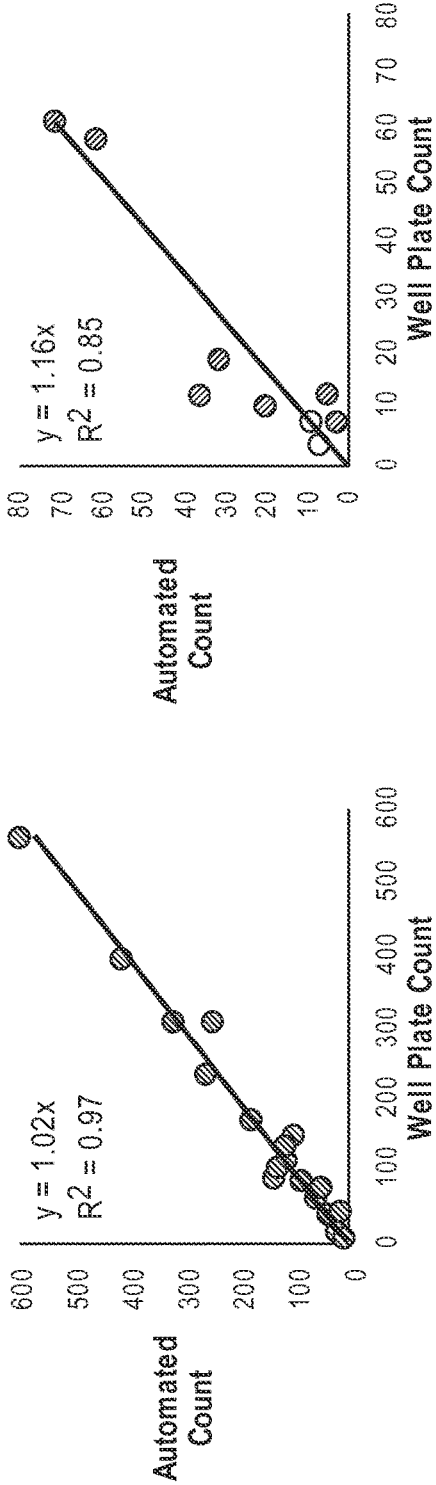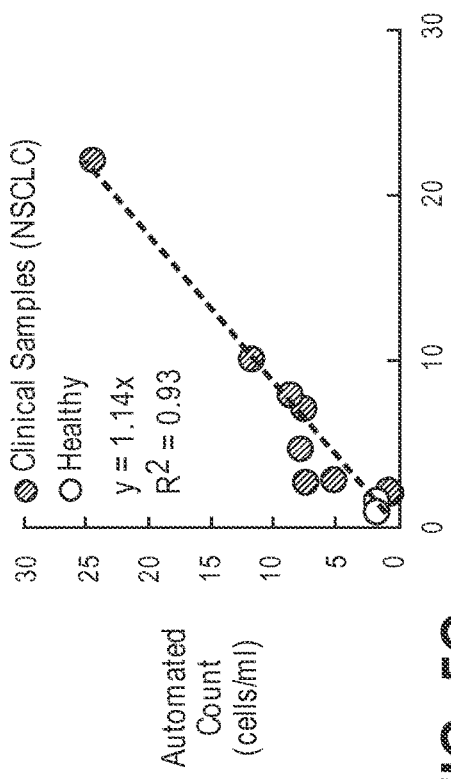
FIG. 5A
FIG. 5B
FIG. 5C

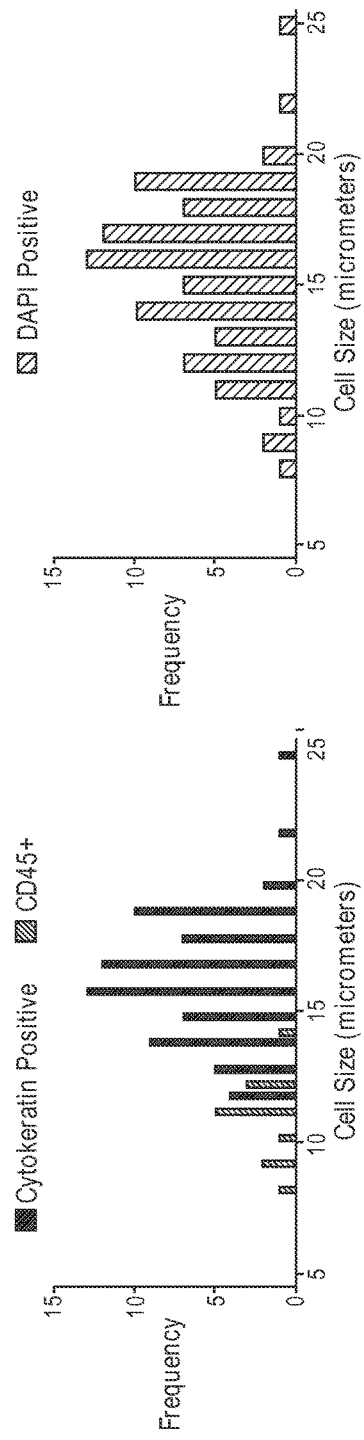

APPARATUS AND METHOD FOR LABEL-FREE ANALYSIS OF RARE CELLS FROM BODILY FLUIDS

RELATED APPLICATION

This Application is a U.S. National Stage filing under 35 U.S.C. § 371 of International Application No. PCT/US2015/038117, filed Jun. 26, 2015, which claims priority to U.S. Provisional Patent Application No. 62/018,415 filed Jun. 27, 2014. Priority is claimed pursuant to 35 U.S.C. § 119. The above-noted Patent Application is incorporated by reference as if set forth fully herein. Priority is claimed pursuant to 35 U.S.C. § 119 and any other applicable statute.

TECHNICAL FIELD

The technical field generally relates to devices and methods for the isolation and analysis of rare cells found in bodily fluids. For example, the invention relates to devices and methods for the isolation and analysis of circulating tumor cells (CTCs) obtain from a bodily fluid.

BACKGROUND

Cancer cells found in circulation are believed to disseminate from tumors and form secondary sites. These malignant cells, termed circulating tumor cells (CTCs), may provide a vital parameter for cancer detection, staging, and developing treatment for tumor metastasis. However, these cells occur within the body at extremely low frequencies (1-500 CTCs/mL blood) and exist among billions of other blood cells (e.g., red blood cells, RBCs, and white blood cells, WBCs), which has motivated methods to achieve efficient isolation for subsequent analysis by targeting specific biomarkers. Larger cell size (>15 μm) compared to normal blood cells, for example, is a characteristic of certain cancers (e.g., non-small cell lung cancer, NSCLC) that allows specific targeting of CTCs from contaminating blood components. The standard mode of analysis is detection with immunostaining (e.g., DAPI positive, EpCAM positive, Cytokeratin positive, and CD45 negative) and enumeration, where a high EpCAM+ CK+ CD45− count has been found to correlate with disease progression and can be used to monitor treatment efficacy. However, the presence of CK+ cells in patients with benign disease and the intra and inter-tumor heterogeneity of both EpCAM and cytokeratin expression indicates the need to analyze other parameters that may correlate more accurately with malignancy.

Traditional methods for cell analysis and counting involve manual measurements, including hemocytometers to determine sample concentrations and microscope graticules for cell size measurements. These processes have become more automated with the discovery of the Coulter principle, which involves detecting events of electrical impedance changes and subsequent correlation to total count and particle size. This is the basis of the Coulter Counter, which is a current standard for cell enumeration and size measurements in laboratory settings. However, the Coulter Counter has a limited window of specificity, which makes it inaccurate in detecting the low frequency of these potentially malignant cells. Additionally, the complex nature of biofluids, which contain a high level of background components, makes it difficult to detect these rare cells of interest. The Coulter Principle also enabled flow cytometry, which is a gold standard for cellular analysis in clinical practice and basic science research. These systems can enumerate and measure cell morphological properties as well as molecular characteristics but are limited by their complexity and high-cost. As with the Coulter Counter, the scarcity of these target cells limits the use of traditional flow cytometers, which require at least tens of thousands of cells per sample and frequencies above ~1% to surpass intrinsic noise.

Immunostaining methods can be used for identifying and analyzing rare cells from bodily fluids. Isolated cell samples are manually manipulated with a series of wash, labeling, and incubation steps to discern captured CTCs from contaminating blood components. Standardized stains such as DAPI (targeting DNA), CD-45 (targeting leukocytes), and cytokeratin (targeting epithelial cells) are used for analysis with fluorescence microscopy. Cells that have a DAPI and cytokeratin signal are defined as CTCs and are differentiated from white blood cells, which have a DAPI and CD-45 signal. Immunostaining and fluorescence microscopy enable detection and enumeration, but require time-consuming protocols to be performed by trained technicians as well as antibodies, which are often expensive and introduce significant variability in performance. These techniques are mostly used because the purity of CTC samples can be low, and allow improved classification accuracy. Additionally, these protocols may require red blood cell lysis, fixation, permeabilization and antibody binding reactions, which alter the native state of the cell population and limit the ability to perform further assays. Further, the label-based method is also limited by inter and intra-tumor heterogeneity, as cells within a single tumor and between different tumor types have different expression levels of these markers.

SUMMARY

In one embodiment, a label-free method for analyzing rare cells from bodily fluids is disclosed. The method uses an upstream microfluidic label-free purification or enrichment device that enriches a population of target cells. In one preferred embodiment, the label-free purification or enrichment device includes a microfluidic channel or multiple microfluidic channels arranged in parallel that contains a plurality of expansion regions located at selected points along the length of the microfluidic channel(s). The expansion regions provide an abrupt increase in the width of the microfluidic channel that, at or above certain flow rates, create a detached boundary layer that causes the formation of vortices within each expansion regions. The vortices created within the expansion regions trap a target population or subpopulation of un-labeled cells from a solution containing heterogeneous cells traveling through the device. The enriched target cells are then released from the expansion regions by reducing or completely eliminating flow through the microfluidic device. The released enriched target cells can then be selectively analyzed downstream from the expansion regions using any one of a number of analysis modalities that analyze cells in a label-free manner. Analysis may be performed, for example, using image frames that are obtained with a high-speed camera and then subject to image processing to measure cell size and/or cell morphology. Analysis may also be performed using a laser interrogation that detects the diffraction or the scattering of laser light from incident cells in a flow using a detector such as a photomultiplier tube (PMT). Another analysis technique that may be integrated includes the use of electrodes in a downstream flow path to measure changes in electrical impedance corresponding to cell volume and conductivity.

Samples obtained from a variety of bodily fluids such as urine, blood, and pleural fluid may be run through the device.

The approach, when coupled with a highly purifying label-free device eliminates the need for antibodies. Furthermore, the analysis method is label-free and enables downstream collection of live cells for further testing, such as cytological analysis, immunofluorescence analysis, cytogenetics, and molecular analysis or even cell growth and drug assays. The resulting platform provides the ability to perform low cost, label-free assays by enriching a sub-population of cells and analyzing parameters such as cell count, cell size, and cell shape, which can be used to help identify malignancies and/or suggest that further analysis are recommended or needed. Additionally, the system's low-cost and fully automated capabilities enable its use in clinical settings. Physicians or lab technicians simply input a blood sample and retrieve information that may correlate with malignancy, which can help guide clinical decision-making.

In one embodiment, a system for the label-free analysis of cells includes a pumping device coupled to a fluid sample containing a heterogeneous population of cells. The system includes a purification device configured to receive the heterogeneous population of cells, the purification device having an inlet coupled to the pumping device and further coupled to a plurality of microfluidic channels, each microfluidic channel having along a length thereof a plurality of expansion regions, wherein the expansion regions temporarily trap therein a subpopulation of cells from the heterogeneous population of cells in response to flow of the fluid sample within the microfluidic channels. The system includes a cell analysis device configured to perform at least one assessment on the cells of the subpopulation comprising: count cells, measure cell size, and/or measure cell morphology.

In another embodiment, a method for the label-free analysis of cells includes flowing a heterogeneous population of cells within a microfluidic device, the microfluidic device having an inlet coupled to a pumping device and further coupled to a plurality of microfluidic channels, each microfluidic channel having along a length thereof a plurality of expansion regions. A subpopulation of cells from the heterogeneous population of cells is trapped in the plurality of expansion regions in response to flow of the fluid sample within the microfluidic channels. The trapped subpopulation of cells is released from the plurality of expansion regions. The trapped subpopulation of cells are analyzed (either within the plurality of expansion regions or downstream after release), wherein analyzing comprises automatically performing at least one of counting cells, measuring cell size, and measuring cell morphology.

In another embodiment, a method of characterizing the health of a subject from a fluid sample (obtained from a subject) includes flowing the fluid sample containing a heterogeneous population of cells within a microfluidic device, the microfluidic device comprising an inlet coupled to a pumping device and further coupled to a plurality of microfluidic channels, each microfluidic channel having along a length thereof a plurality of expansion regions. A subpopulation of cells from the heterogeneous population of cells is trapped within the plurality of expansion regions in response to flow of the fluid sample within the microfluidic channels. The trapped subpopulation of cells from the plurality of expansion regions is released and automatically counted using a counting device. A characterization of the health of the subject is generated based at least in part on the count of the subpopulation of cells, wherein the health of the subject is characterized as unhealthy when the count exceeds a threshold value.

BRIEF DESCRIPTION OF THE DRAWINGS

FIG. 5A illustrates a graph showing the results of an automated cell count (A549 cells) using the device of FIG. 1A compared a manual cell counting process.

FIG. 5B illustrates a graph showing the results of an automated cell count (NSCLC patient samples and two (2) healthy samples) using the device of FIG. 1A compared a manual cell counting process.

FIG. 5C illustrates a graph illustrating the automated cell count using concentration of cells (cells/ml) for NSCLC patient samples (9) and two (2) healthy samples using the device of FIG. 1A compared a manual cell counting process.

FIG. 6A illustrates the results of cell size frequency measurements from cell samples isolated at high purity levels from patient bodily fluids using the purification device of FIG. 1A.

FIG. 6B illustrates the results of the same cell size frequency measurements of FIG. 6A wherein all of the cells that were obtained from the purification device where stained with DAPI.

DETAILED DESCRIPTION OF THE ILLUSTRATED EMBODIMENTS

Figure 1A:
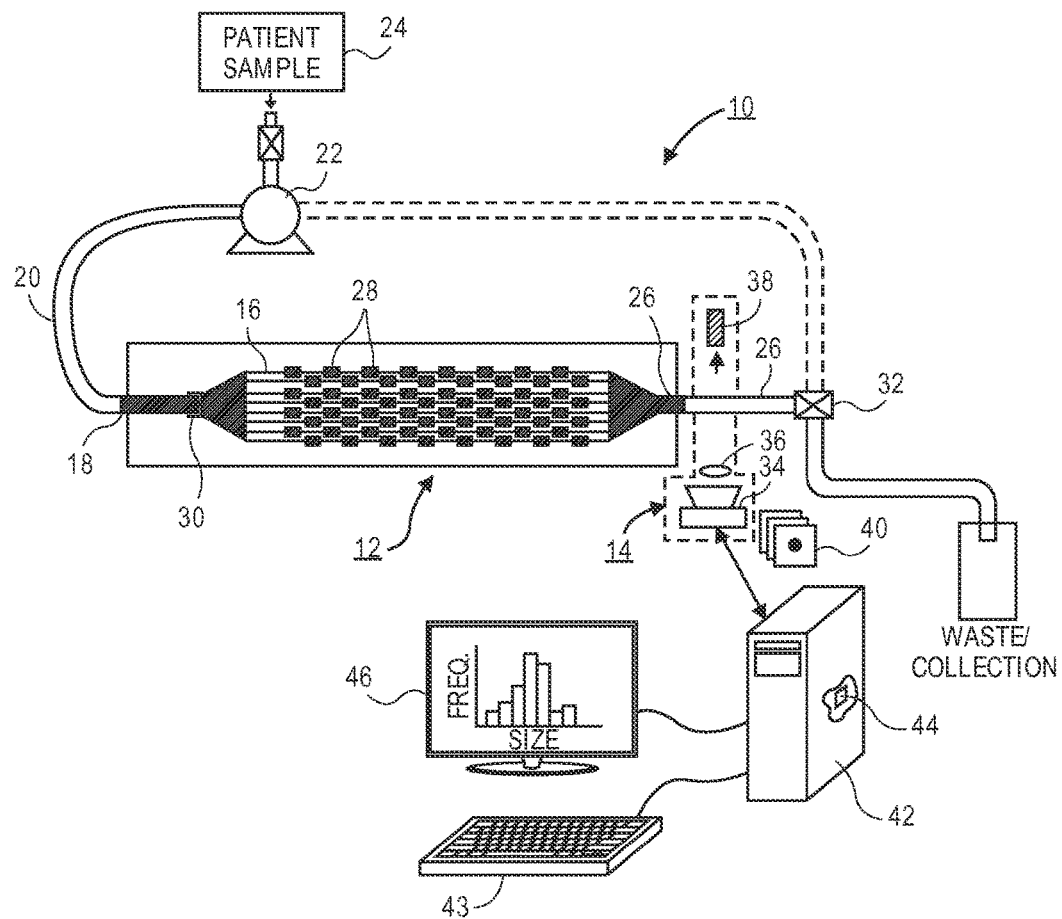
FIG. 1A is a schematic representation of the system for the automated, label-free analysis of rare cells from bodily fluids according to one embodiment.

FIG. 1A illustrates a schematic representation of a system 10 for the automated, label-free analysis of rare cells from bodily fluids according to one embodiment. The system 10 includes an enrichment or purification device 12 along with a cell analysis device 14. In one preferred embodiment, the purification device 12 is a microfluidic device that is located upstream of the cell analysis device 14. In the embodiment of FIG. 1A, the purification device 12 includes at least one microfluidic channel 16 coupled to an inlet 18. The inlet 18 is connected to a conduit or tubing 20 that connects to a pump 22. The pump 22 is connected to a source of or otherwise contains a patient sample 24 (e.g., syringe pump loaded with a syringe containing the patient sample 24). The patient sample 24 is a fluid and can be, for example, blood, urine, pleural fluid, and peritoneal fluid. The pump 22 can be a pump such as a syringe pump, or pressure source controlled with a regulator, although other pumps commonly used in microfluidic applications may be used.

The purification device 12 is typically made from using standard photolithography or other manufacturing techniques used in microfluidic devices. The purification device 12 may be made of any number of substrate materials such as, for example, silicon, glass, polymers or plastics (e.g., cyclic olefin polymer (COP), cyclic olefin copolymer (COC), polycarbonate (PC), Poly(methyl methacrylate) (PMMA), Polydimethylsiloxane (PDMS)). In the embodiment of FIG. 1A, eight (8) separate channels 16 each coupled at respective ends to the inlet 18 and a common outlet 26. While eight (8) channels 16 are illustrated, different numbers of channels 16 can be used as well. The microfluidic channels 16 act as focusing microchannels 16. Each separate microfluidic channel 16 has eight (8) expansion regions 28 serially arranged along the length of the microfluidic channel 16 although different numbers of expansion regions 28 can also be employed. Preferably, the at least one microfluidic channel 16 has a height, in the out of plane direction, within the range of 40-80 µm and a width less than 40 µm and an aspect ratio defined by the ratio of height to width of >1.5. A plurality of expansion regions 28 are disposed along the length of each microfluidic channel 16, wherein each of the plurality of expansion regions 28 is an abrupt increase in the width of the at least one microfluidic channel 16, wherein the width of each expansion region 28 is at least 480 µm and lasts for at least 720 µm along a length of the expansion region 28, followed by an abrupt decrease in the width of the expansion region 28 back to height within the range of 40-80 µm and a width less than 40 µm.

In one embodiment, the purification device 12 may be in the form of a microfluidic chip that is available from Vortex BioSciences, Inc. (Palo Alto, Calif.). The expansion regions 28 provide an abrupt increase in the width of the microfluidic channel 16 that, at or above certain flow rates, create a detached boundary layer that causes the formation of vortices within each expansion region 28. The vortices created within the expansion regions 28 trap a target population or subpopulation of cells from a solution containing heterogeneous cells traveling through the device. The subpopulation that is trapped is based on the size of the cells. Larger cells get trapped within the expansion regions 28 while smaller cells continue through the device. A device with such expansion regions is described in U.S. Patent Application Publication No. 2013/0171628, for example, which is incorporated by reference herein.

Figure 1B:
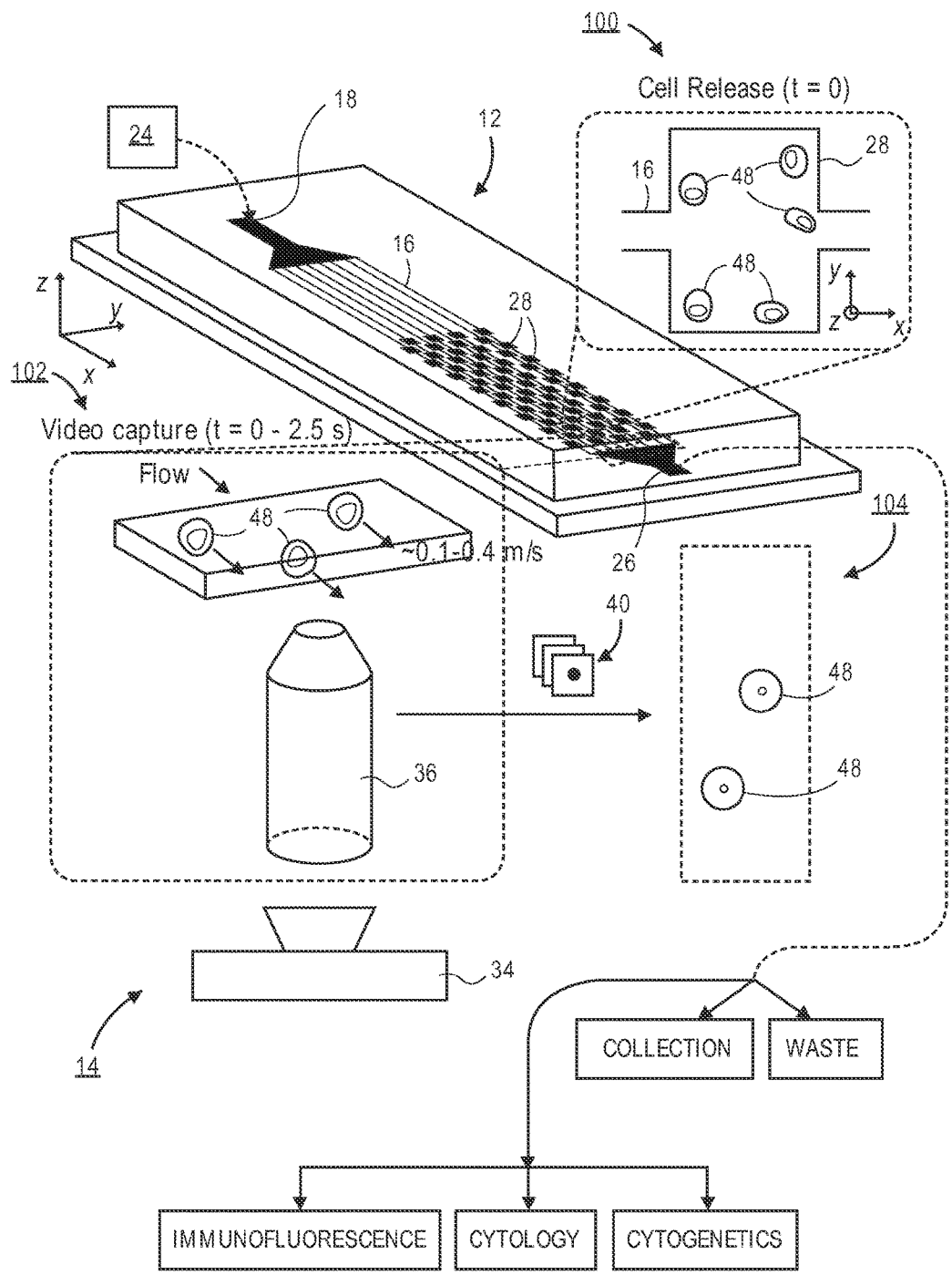
FIG. 1B is a schematic representation of the operations involved in the embodiment illustrated in FIG. 1A.

Still referring to FIG. 1A, the patient sample 24 is a fluid that contains a heterogeneous population of cells, namely, cells of different phenotypes. The pump 22 then pumps this patient sample 24 into the inlet 18 of the purification device 12. The purification device 12 may optionally include a filter 30 or the like to filter out large particles or contaminants. During use, a subpopulation of cells 48 (as seen in FIG. 1B) from the heterogeneous population of cells is temporarily trapped within the expansion regions 28. In one aspect, the subpopulation of cells 48 that is trapped within the expansion regions 28 is defined by the size of the cells. For example, in one aspect of the invention, cells having a size at or above a pre-determined cutoff range are trapped within the expansion regions 28 while cells having a size below the threshold pass through the device 12 without being trapped. Larger cells (e.g., cancer cells), for instance those above 10 µm, could remain trapped within the purification device 12 and then selectively eluted for subsequent analysis. Non-trapped cells such as red blood cells (RBCs) and smaller sized white blood cells (WBCs) can pass through the purification device 12 without being trapped thereby enriching or purifying the trapped cells. As seen in FIG. 1A, cells passing through or by the cell analysis device 14 leave via the outlet 26. A valve 32 may be used to direct these cells to waste or collected receptacle, or even continued downstream processing. For example, cells could be collected or passed to one or more downstream devices for additional cytological analysis, morphological analysis, molecular analysis, drug assay testing, nucleic acid sequencing, or cell growth. FIG. 1B illustrates that cells 48 may be subject to further analysis such as immunofluorescence, cytology analysis (with papanicolaou stain), and cytogenetics with FISH. Alternatively, the fluid (and cells 48) that pass through the outlet 16 may be recirculated back to the pump 22 and into the purification device 12.

Once the subpopulation of cells 48 is trapped in the expansion regions 28, the cells 48 of this subpopulation may be released for downstream analysis by the cell analysis device 14. Release of the cells 48 from the expansion regions 28 may be controlled by adjusting the flow rate of the fluid being pumped through the purification device 12. For example, the purification device 12 may operate at a variety of flow rates but a flow rate of 4 mL/min has been found to work well. Release of the subpopulation of cells 48 is accomplished by rapidly decreasing the flow rate, for example reducing the flow rate to a very slow rate or even zero (0) ml/min. In some devices, there is some capacitive flow that exists within the microfluidic channels 16 even if the flow is completely stopped. This capacitive flow is enough to push the cells 48 downstream into the cell analysis device 14.

In one preferred aspect, the purification device 12 and/or cell analysis device 14 are implemented in a microfluidic platform or multiple microfluidic platforms that are integrated together. For example, the purification device 12 could be a microfluidic chip in which cells are input into the device whereby larger sized cells are selectively trapped therein. The trapped cells 48 can then be released whereby the cells 48 then travel to a separate cell analysis device 14. The cell analysis device 14 may, in some embodiments, only count cells 48 passing thereby. In other embodiments, the cell analysis 14 may count cells 48 as well as determine one or more morphological parameters for the cells 48. This can include cell size, cell circularity, cell aspect ratio, cellular granularity, blebbing, membrane roughness, nuclear shape, and the like. In an alternative configuration, part of or the entire cell analysis device 14 may be integrated with the purification device 12. For example, a downstream portion of the purification device 12 may include an imaging region that is imaged by the cell analysis device 14. For example, the outlet 26 of the purification device 12 may include a cell analysis region that is used to image or otherwise analyze cells that pass thereby.

FIG. 1A illustrates an embodiment of the system 10 that uses a high speed camera imaging system as the cell analysis device 14. The cell analysis device 14 includes a high speed camera 34 in conjunction with a lens 36 (or combination of lenses) that is used to image a portion of the outlet 26 of the purification device 12. A light source 38 is used to provide illumination of the field to image the passing cells. Cells traverse this region at speeds of 0.1-0.4 m/s, which depends on the time after release. The captured high-speed video, which is taken at a suitable frame rate to generate image frames 40 to either capture one or multiple measurements per cell, can then be analyzed with the custom automated script, as described below. In one implementation, this system 10 requires interfacing a high-speed camera 34 coupled to a 10X or 20X objective lens 36 (Nikon CFI Plain Fluor 10× & 20×) and the microfluidic purification device 12. The frame rate requirements of the camera 34 depend on the resolution of the imaging area, but with the purification device of FIG. 1A, for example, a 500 fps frame rate is needed for a 256 pixel×376 pixel imaging area. Alternatively, a frame rate of 5000 fps will enable multiple measurements per cell for a 144 pixel×376 pixel imaging area. The requirements for this allow the use of commercially available low cost off-the-shelf cameras (e.g., Casio EX-F1, JVC GC-PX100). Cells 48 are analyzed during their release step from the purification device 12, which occurs when the flow is slowed significantly or stopped. With the chip of FIG. 1A, cells 48 pass through this imaging area at around 0.2 m/s when the flow rate is reduced to 0 mL/min from its optimal flow condition at 4 mL/min. In the event the number of microfluidic channels 16 is doubled to sixteen (16) channels, the optimal flow conditions are at an increased rate of 8 mL/min for trapping. The acquired video is then analyzed through an automated script to extract a total cell count and cell morphology measurements. Image sequences are recorded using the high-speed camera 34 and the Phantom Camera Control Software (Vision Research, Inc.).

Still referring to FIG. 1A, the camera 34 is connected via a wired or wireless connection to a computer 42 containing one or more processors 44 therein. The computer 42 may include a personal computer, laptop computer, server, or even a tablet or other portable based computer. The computer 42 may include one or more input devices 43 like a keyboard, mouse or the like. Image frames 40 captured by the camera 34 are then transferred to the computer 42. Image transfer may take place as a sequence of frames as part of a continuous movie file or they may include images taken over periodic time intervals. The computer 42 contains software loaded thereon that is used for image processing of the image frames 40. The results of the image analysis may be presented to the user using, for example, a display 46 that is associated with or otherwise connected to the computer 42. An example of image processing software that is executed by the one or more processors 44 includes MATLAB although other image processing programs may also be used. The image processing software is used to identify and count the number of cells 48 of the subpopulation that pass by the field of view of the camera 34. The counting process involves identifying the number of cells 48 in the field of view using a background subtraction process as described in more detail below. In addition to counting the cells (or other particles), the software executed by the processors 44 is used to determine the size of the cell as well as the morphology of the cell. The morphology of the cell includes such parameters as circularity, aspect ratio, granularity, blebbing, membrane roughness, nuclear shape, and the like.

FIG. 1B illustrates the manner in which the embodiment of FIG. 1A operates. The purification device 12 is illustrated as well as the cell analysis device 14 which in this embodiment includes a lens 36 and camera 34. First, in step 100 the trapped subpopulation of cells 48 is released from the expansion regions 28 by significantly reducing or stopping flow through the purification device 12. The time of release is referred to as t=0. The cells 48 of the trapped subpopulation then leave the expansion regions 28 and travel downstream through the purification device 12. As seen in step 102, image frames 40 are captured using a camera 34. The image frames 40 are captured as a continuous movie or periodically obtained image frames 40. The video or image capture step 102 occurs within about 0 to 2.5 seconds after release of the cells from the expansion regions 28. FIG. 1B also illustrates step 104 where the captured image frames 40 undergo image processing. In FIG. 1B two cells 48 are identified in the image frame 40. The two cells 48 are cells from the trapped subpopulation of cells that were released downstream in the purification device 12 by stopping or significantly reducing the flow rate through the purification device 12.

Figure 1C:
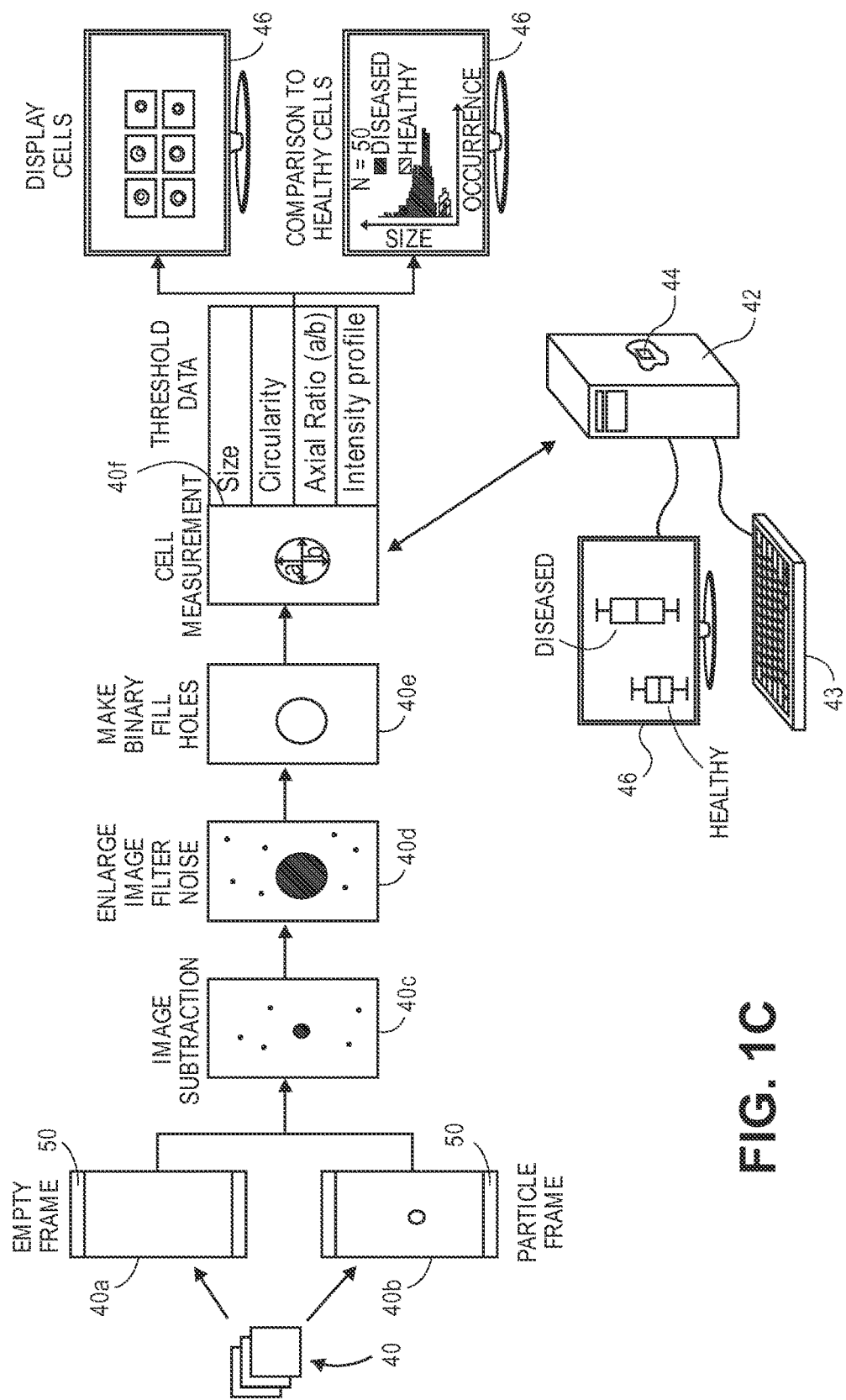
FIG. 1C is an illustration of the image processing steps used to count and measure cells using the embodiment of FIG. 1A.

FIG. 1C graphically illustrates how the MATLAB-based custom-built code that reads through image frames 40 of a captured video segment and returns cell count, size, and morphology measurements. FIG. 1C illustrates an empty image frame 40a that contains no cells and an image frame 40b that contains a particle or cells. First, the channel walls 50 of the purification device 12 (e.g., outlet 26) are cropped from every frame of the captured video to avoid any errors during cell detection and measurement. This includes removing the channel walls from the empty image frames 40a and the cell-containing image frames 40b. In one aspect of the invention, 256 pixel by 376 pixel image frames 40 are captured every 2 milliseconds to gain one measurement per particle/cell. Of course, the size of the image frame 40 and the speed at which the image frames 40 are obtained can be changed. For example, the image parameters can be tuned so that image frames 40 are captured every 0.2 milliseconds at a resolution of 144 pixel by 376 pixel, enabling multiple measurements per incident particle/cell. Next, using a background subtraction method, the intensity values of an empty frame 40a are subtracted from each ensuing image frames 40a, 40b of the video, which eliminates the background image and yields traces (i.e., outlines of the particles cells) of the particles or cells 48 present in the image frames 40 in which they appear. FIG. 1C illustrates a background-subtracted image frame 40c that has been subject to the background image subtraction process.

Next, the resulting image frames 40c are resized 3x to increase the accuracy of measurements to sub-micron resolution and noise is filtered out to produce an enlarged image frame 40d. After this step, the image frames 40d are converted to a binary format and the cell traces are filled with morphological closing using an erosion process followed by dilation as seen in image frame 40e. This image frame 40e is then used for cell measurements as seen in image frame 40f where the major axis (b) and the minor axis (a) are shown on the filled cells. Using image frame 40f, various morphology properties can be measured or otherwise calculated. These include cell size, cell circularity, axial ratio (a/b), and intensity profile. Circularity is calculated using software executed on the computer 42 according to the formula $4\pi A/L$ where A is the cell area and L is the cell perimeter. The process continues for each next frame 40 that was captured by the camera 34 until all released cells 48 are counted or otherwise analyzed. As explained below, the results can be plotted as a size histogram 52 and compared to data from healthy patients, which can reveal abnormalities that correlate to disease state and the need for further diagnostic analyses.

FIG. 1C illustrates a size histogram 52 that measures the frequency of different sizes of cells 48 for the patient sample 24 that were imaged using the cell analysis device 14. Note that this size histogram 52 also is overlaid with the corresponding histogram of cells 48 obtained from a healthy subject. Thus, the frequency or distribution of the size of the cells 48 from the subpopulation can be compared to existing data obtained from healthy subjects. Cell size distribution data from healthy subjects can be stored or otherwise accessed by the software running on the computer 42 and compared with the data that has been obtained using the system 10. For example, FIG. 1C illustrates a comparison graph 54 that shows the size distribution of the cells 48 within the patient sample 24 as compared to the size distribution of cells 48 obtained from a healthy subject (or multiple healthy subjects). In this particular example, the sizes of the cells 48 obtained from the cancer patient sample 24 are generally larger in size than those from a healthy subject. This comparison can then be used to automatically generate diagnostic outcomes for the patient providing the sample 24. For example, when the distribution of measured size of cells 48 (or other morphological parameter) is above a threshold level when compared to a healthy subject, this can be used to automatically flag the sample 24 as potentially cancerous. Various statistical parameters could be used for this threshold. This may include, for example, deviance from an average or mean value as compared to a healthy subject's sample or other statistical measurement such as standard deviation. Values may include absolute numbers of cells or cell concentration in the sample as described below.

Counts above a cut-off on this histogram can be indicative of disease in a patient (e.g., cancer, leukemia, etc.), and be diagnostically useful in a screening role to indicate that additional imaging or testing is warranted. For example, counts of large cells with a diameter above a cut-off value of 12 micrometers and below 50 micrometers, circularity ranges from 0.7 to 1, and axial ratio ranges from 0.8 to 1.8, were counted as shown in FIGS. 5A, 5B, and 5C. FIG. 5C illustrates a graph illustrating the automated cell count using concentration of cells (cells/ml) for NSCLC patient samples (9) and two (2) healthy samples using the device of FIG. 1A compared a manual cell counting process. Table 1 below illustrates the cell counts, calculated cell concentrations, and sample volumes for each sample.

TABLE 1

| Patient ID | Well Plate (# cells) | Automated (# cells) | Well Plate (cells/mL) | Automated (cells/mL) | Volume (mL) |
|---|---|---|---|---|---|
| 072914-JG1-4 | 19 | 31 | 5 | 8 | 4 |
| 013114-EG1-2 | 13 | 36 | 3 | 7 | 5 |
| 020515-EG1-2 | 8 | 3 | 2 | 1 | 4 |
| 032515-JG1 | 11 | 20 | 3 | 5 | 4 |
| 040915-JG1 | 61 | 71 | 10 | 12 | 6 |
| 050714-EG1-6 | 13 | 5 | 2 | 1 | 6 |
| 52115-JG1 | 58 | 61 | 7 | 8 | 8 |
| 040915-JG1-2 | 44 | 49 | 22 | 25 | 2 |
| 062014-JG1-7 | 24 | 26 | 8 | 9 | 3 |
| 031715-H1 (healthy) | 8 | 9 | 1.6 | 2 | 5 |
| 032615-H2 (healthy) | 4 | 7 | 1 | 2 | 4 |

Figure 6C:
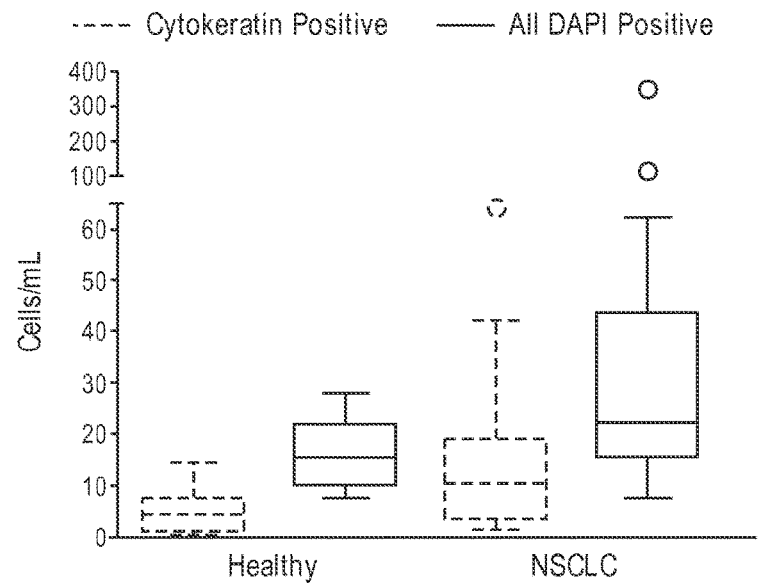
FIG. 6C illustrates the immunofluorescence analysis of patient samples (NSCLC) which reveal an increase of cytokeratin positive cells compared to healthy samples, which can also be seen when looking at all of the captured cells as represented by the DAPI positive cells.

Counts that exceed a threshold of 2 cells/mL were indicative of patients with non-small cell lung cancer. To increase specificity of the assay, larger cut-off thresholds could be used, for example, 5, 10, or 20 cells per mL. Alternatively, all of the cells that are trapped and released by the upstream microfluidic separation system can be counted, and a threshold on all isolated larger cells that are counted can be used to indicate health. In this particular example, only counting of the cells that are released is required. Threshold values in this case of 30 to 50 cells per mL can be used to evaluate whether the patient is positive for NSCLC (FIG. 6C). It should be understood that other parameters beyond size and different threshold values can be used to adjust the sensitivity and specificity of the assay to detect disease by using the large cell count from blood (or other body fluids). For example, unhealthy (e.g., diseased cells) may be determined based on other morphological parameter such as, deformability, circularity, shape, aspect ratio, granularity, roughness, blebbing extent, nuclear shape, and the like. A diagnosis of cells based on a threshold or range of the above-noted parameters may likewise be used.

Figure 1D:
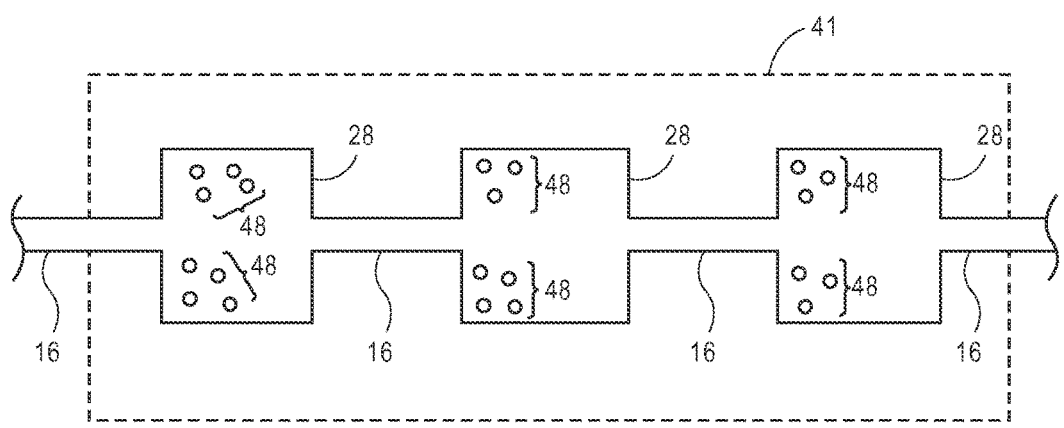
FIG. 1D illustrates an alternative embodiment of the invention in which cells are imaged in the expansion regions.

While FIG. 1A illustrates an imaging region that is located downstream with respect to the purification device 12 it should be understood that the imaging region may be located within the purification device 12. For example, the expansion regions that contain the trapped sub-population of cells 48 may be imaged using a wide field-of-view imager or a scanning device to capture images of trapped cells. These images can then be used to count cells, measure cell size or other morphological parameters of the trapped cells. Preferably, this imaging process is conducted following a rinse step to remove smaller non-target cells (e.g. red and white blood cells). For example, FIG. 1D illustrates an example of an embodiment where the imaging field-of-view 41 of, for example, a camera 34 encompasses the expansion regions 28. In this embodiment, the cells 48 can be counted while they are trapped in the expansion regions 28. There is no need to release the cells 48 for downstream imaging as the imaging takes place during the trapping step. This embodiment may employ similar image processing techniques as those described above in the context of FIG. 1C. Here, however, the image frames 40 will contain multiple cells which are identified and counted by imaging software. Similar size and morphological measurements may be made of the cells 48 that are trapped in the expansion regions 28.

Given the wider field-of-view 41 as seen in FIG. 1D, the camera system used in this embodiment should have a wide field-of-view with low magnification. A strobed light source or a camera with fast exposure time can be used after a washing step has removed any residual white or red blood cells. An alternative imaging system that can be used to image cells 48 while they are trapped within the expansion regions 28 includes so-called lens-free imaging systems that use a light source to generate hologram images of small particles such as cells and high-resolution images are reconstructed using phase and amplitude information contained in the holographic images.

Figure 2:
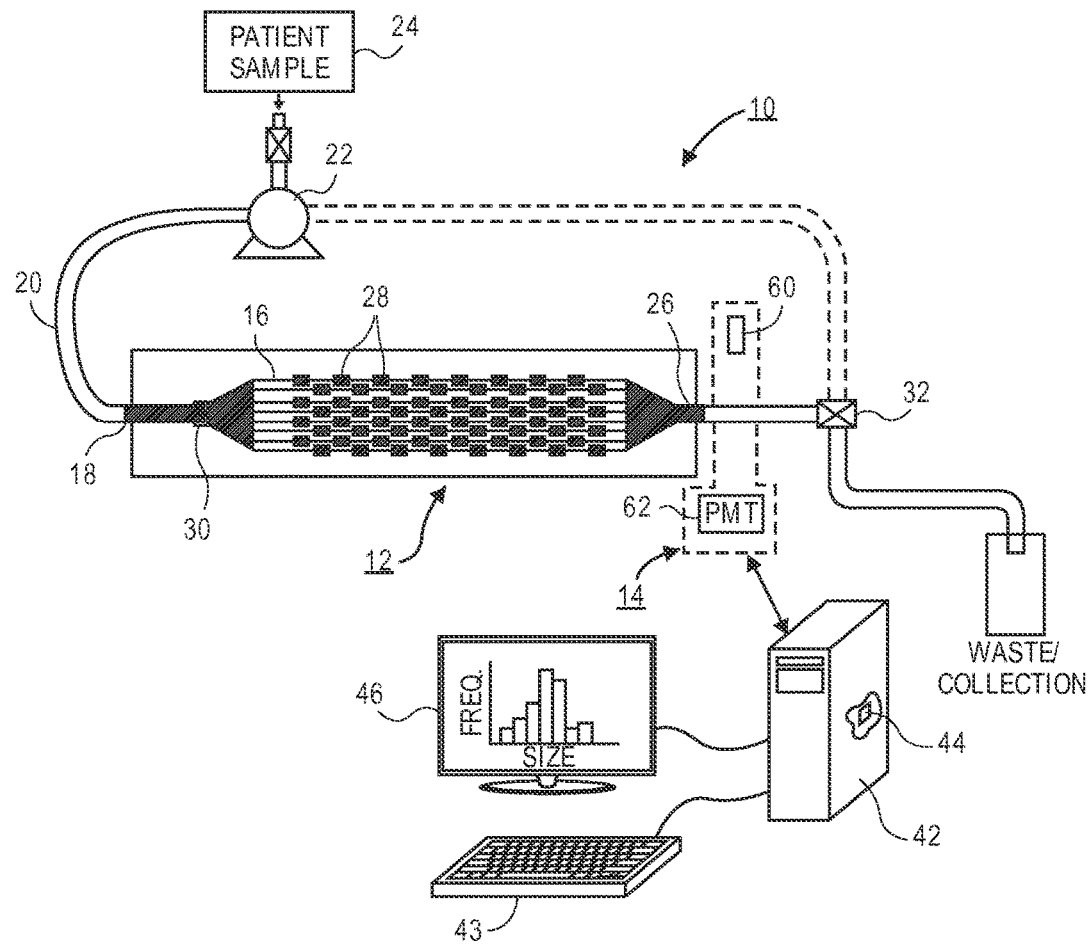
FIG. 2 illustrates another embodiment of a system for the automated, label-free analysis of rare cells from bodily fluids. This embodiment uses a laser light source and one or more PMTs or photodiodes to detect scattered light.

FIG. 2 illustrates another embodiment of system 10 for the automated, label-free analysis of rare cells from bodily fluids. Equivalent features as those illustrated in the embodiment of FIG. 1A are labelled similarly. In this regard, the system 10 uses a purification device 12 as explained previously to purify or enrich a subpopulation of cells 48 from a heterogeneous population. In this alternative embodiment, however, the cell analysis device 14 uses a laser light source 60 that is directed at the flow path created in the common outlet 26 or at a downstream region within the purification device 12 itself. The laser light source 60 illuminates the flow path at one or more angles and scattered light is captured with a photomultiplier tube (PMT) or multiple PMTs. Alternatively, a photodiode detector may also be used to detect scattered light. Optical fibers may be connected to the laser light source 60 provide for multi-angle illumination of the flow path. As a cell 48 passes through the laser beam, light is scattered and the manner in which light bounces of the cell 48 or other particle provides information on the cell's 48 characteristics. For example, scattered light may be collected at two angles: a forward scatter and a side scatter. Additional scattered angles may also be employed. For example, forward scatter may be used to determine the cell size while the side scatter channel may be used to measure granularity of the cell 48. When scattered light hits the PMT or photodiode are converted to a voltage pulse. These analog voltage pulses are amplified by the PMT or an outside amplifier. The analog signals are typically converted to digital values by an analog-to-digital converter (ADC). Pulse shape analysis performed by the computer 42 is able to determine the characteristics of the cell 48 as it passes through the laser beam. The results of the characterization may be used for cell count purposes as well as information regarding the morphology of the cell 48 (e.g., circularity and granularity).

Figure 3A:
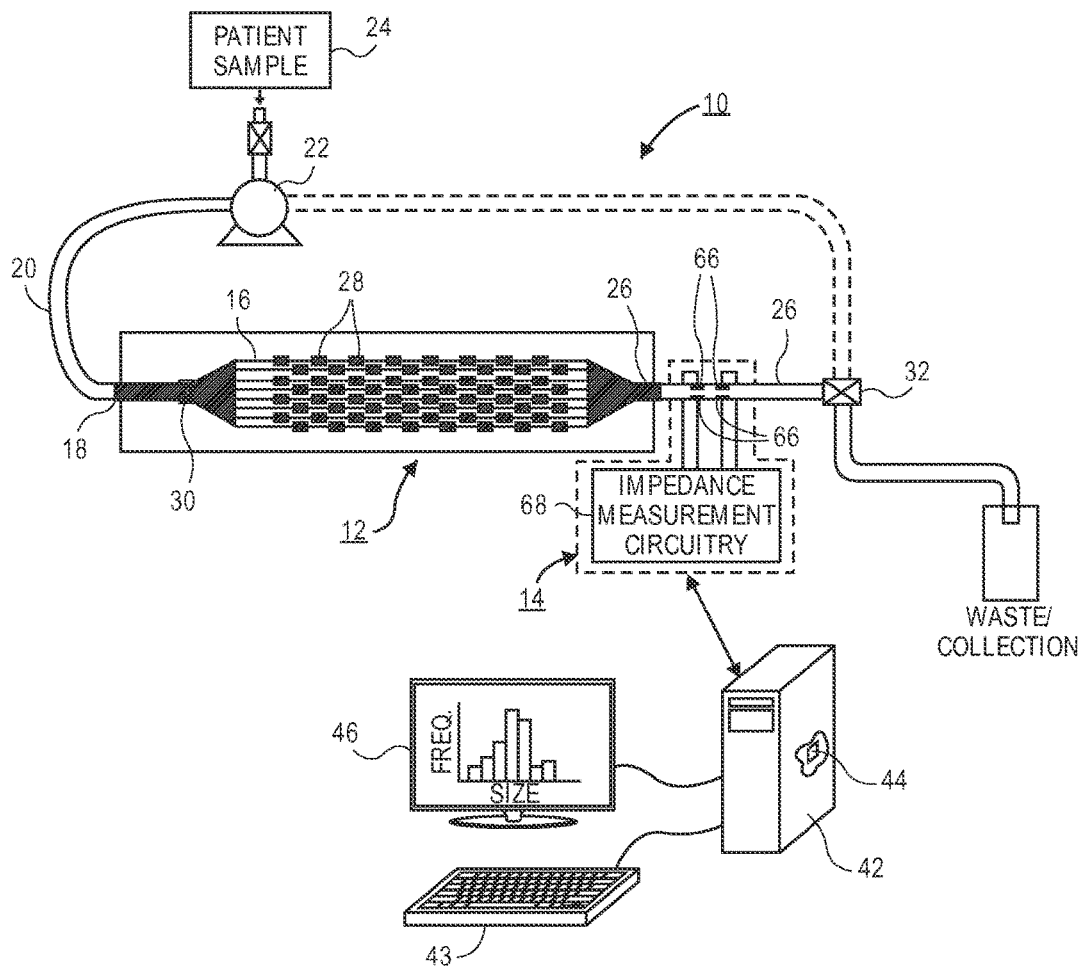
FIG. 3A illustrates another embodiment of a system for the automated, label-free analysis of rare cells from bodily fluids. This embodiment uses electrodes and impedance measurement circuitry to count as well as detect morphological parameters of cells released from the upstream purification device.
Figure 3B:
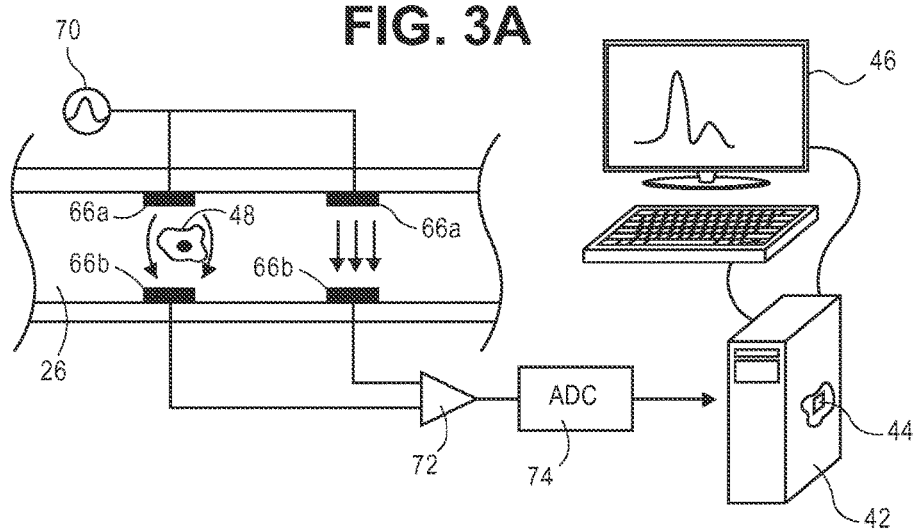
FIG. 3B illustrates aspects of the impedance measurement circuitry according to one embodiment.

FIGS. 3A and 3B illustrate another embodiment of system 10 for the automated, label-free analysis of rare cells from bodily fluids. Equivalent features as those illustrated in the embodiment of FIG. 1A are labelled similarly. In this regard, the system 10 uses a purification device 12 as explained previously to purify or enrich a subpopulation of cells 48 from a heterogeneous population. In this alternative embodiment, however, the cell analysis device 14 uses electrodes 66 and impedance measurement circuitry 68. In this embodiment, as best seen in FIG. 3B, a function or signal generator 70 is used to apply an AC signal to excitation electrodes 66a as seen in FIG. 3A. One or more sensing electrodes 66b located along an opposing surface of the microfluidic channel 16 or the common outlet 26 are used to sense the measured impedance. The voltage signals picked up by the sensing electrodes 66b may be amplified with an amplifier 72 and converted to a digital signal by a ADC 74. The impedance measurement circuitry 68 may be located outside of the computer 42 or it may be integrated therein, for example, on a dedicated card or board installed in the computer 42. The impedance measurement circuitry 68 is used to measure the impedance frequency response changes that occur when a cell 48 passes by the electrode(s) 66. This response can be used to count cells as well as determine morphological parameters (e.g., size and shape, circularity, deformability, viability). The impedance response of passing cells 48 may be correlated, for example, to a library of data stored in the computer 42 that can be used to predict the size and morphology of the passing cells 48. As noted herein, this is embodiment is different from the standard Coulter counter device which requires large numbers of cells per sample and typically uses DC or low-frequency signals for cell size characterization.

Figure 4:
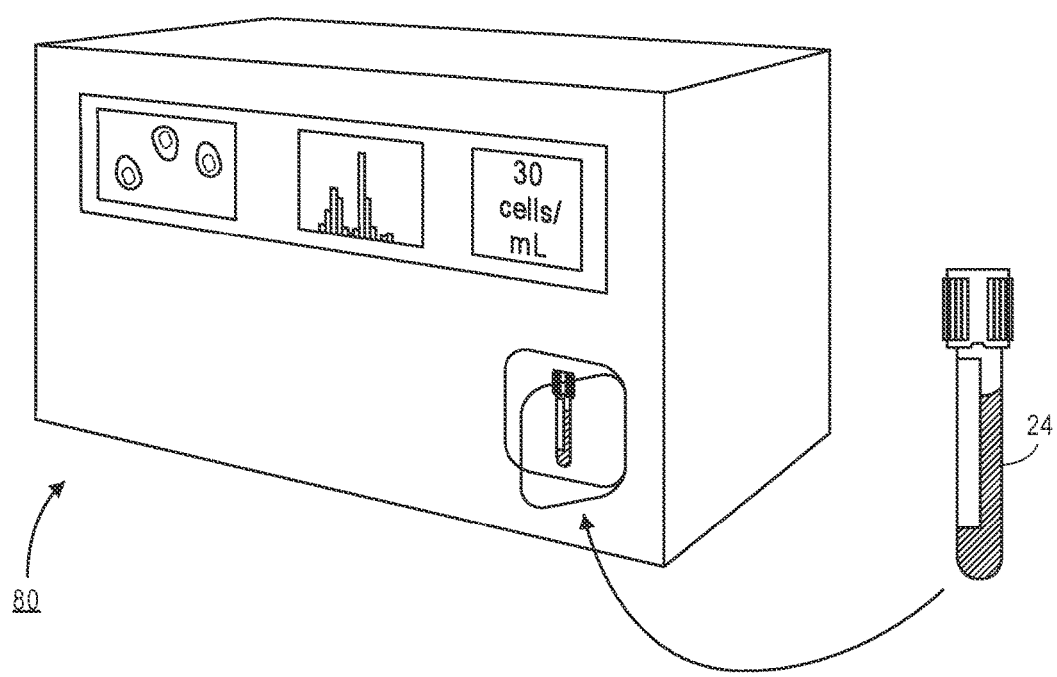
FIG. 4 illustrates an embodiment of a bench-top type device in which a sample containing a bodily fluid such as blood is inserted into the testing device.

FIG. 4 illustrates an embodiment of a bench-top type device 80 in which a sample containing a patient sample 24 (e.g., bodily fluid such as blood) is inserted into the testing device 80. The device 80 may output a size histogram, or density measurement of cells (cells/mL), ROC curves compared to healthy cells, or even a diagnosis or a recommendation for additional testing. The versatile nature of this system allows its combination at low-cost with cell-sorting devices in a closed system. Full automation also enables adoption into a clinical setting. Cell measurements that may correlate to disease state can be quickly extracted to help improve clinical decision-making. Note that in this embodiment, the purification device 12, cell analysis device 14, computer 42, and display 46 are all integrated into a single device. Unlike the system, for example, illustrated in FIG. 1A, all of the components are integrated into a single system.

FIGS. 5A and 5B illustrate that the in-flow cell counting algorithm or script correlates strongly with a manual counting operation where cells were collected off-chip and counted in a standard well plate. In both the automated and manual counting operations, only cells larger than 12 μm were counted. In the data illustrated in FIG. 5A, A549 cells lines were run through the system illustrated in FIG. 1A and automated cell counts were obtained using the cell analysis device 14 as described herein. Cells were also captured off-chip and counted in standard well plates. FIG. 5B illustrates data of NSCLC patient samples (shaded circles) and two (2) healthy samples (non-shaded circles). Again, only cells larger than 12 μm were counted. As seen in FIGS. 5A and 5B, there is good correlation between the number of cells that were counted using the automated algorithm as compared to the manual counting process.

FIG. 6A illustrates the results of cell samples isolated at high purity levels from patient bodily fluids. In particular, FIG. 6A illustrates size measurements that were obtained of an immunostained cell population (non-small cell lung cancer, NSCLC, patient sample) that were first isolated with the purification device 12 of FIG. 1A. The trapped cells were released and captured off chip where the cells were then stained to identify those cells that are cytokeratin positive and CD45 positive. Cell size was measured manually. Cytokeratin positive cells are large circulating cancer cells while the CD45 positive cells are non-cancerous white blood cells. As seen in FIG. 6A, the collected cells contain a highly pure population of large circulating tumor cells as identified by being cytokeratin positive. Only a small portion of the collected cells were CD45 positive.

FIG. 6B illustrates the results of the same experiment wherein all of the cells that were obtained from the purification device 12 where stained with DAPI. Cell size was measured manually. As seen in FIG. 6B, the size distribution and profile of the DAPI stained cells (which identified all cells) closely matches that seen from FIG. 6A for cytokeratin positive cells. Thus, counting all of the cells within the subpopulation that were trapped and then released enables accurate analysis of the entire cell population without the need for complex, manual, and costly staining. The presence of small numbers of white blood cells as illustrated by the CD45+ stained cells in FIG. 6A means that total cell count and size distribution can be used as a proxy for identifying diseased patient samples (e.g., samples that contain cancer cells).

Figures 6D, 6E:
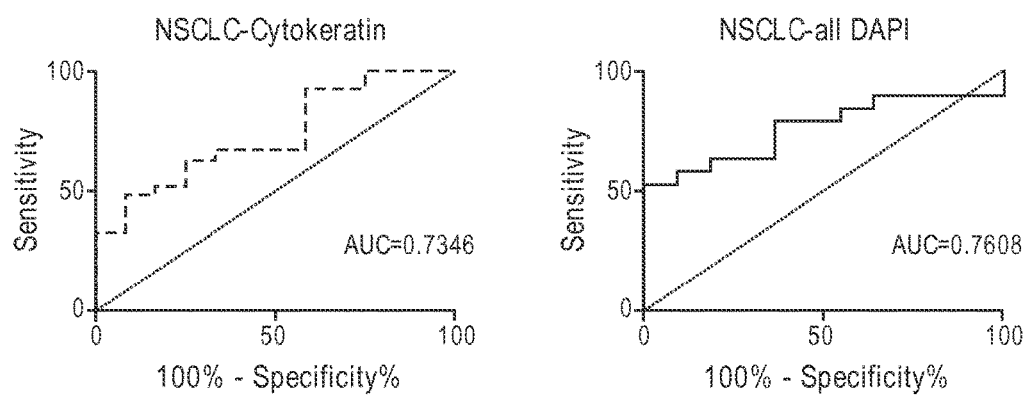
FIG. 6D illustrates the receiver operating characteristic analysis of enumeration from immunofluorescence of NSCLC (e.g., the gold standard) as compared to healthy samples. The area under the curve is 0.7346.
FIG. 6E illustrates the receiver operating characteristic analysis of enumeration from all of isolated cells from NSCLC and healthy samples. The area under the curve is 0.7608.

The data from the entire isolated cell population varies only slightly from the data retrieved through immunofluorescence analysis, thus showing that label-free analyses can achieve similar results as compared to the current "gold standard" tests. FIG. 6C illustrates the immunofluorescence analysis of patient samples (NSCLC) which reveal an increase of cytokeratin positive cells compared to healthy samples, which can also be seen when looking at all of the captured cells as represented by the DAPI positive cells. FIG. 6D illustrates the receiver operating characteristic analysis of enumeration from immunofluorescence of NSCLC (e.g., the gold standard) as compared to healthy samples yields an area under the curve of 0.7346. The analysis of all of isolated cells from NSCLC and healthy samples yields a slightly higher area under the curve of 0.7608 as seen in FIG. 6E, demonstrating that counting all of the cells that have been trapped by the purification device 12; a method that uses the label-free analysis of cells can meet or exceed the benchmark of the current gold standard. The ROC curves also enable the detection of abnormal levels of circulating cells that indicate the need for further analysis (e.g., cytological, molecular, or the like). The system 10 described herein is a label-free system that passively analyzes a population of cells following a high purity label-free cell separation from body fluids (e.g., blood, pleural, urine, peritoneal fluid, etc.). The purification process yields a high purity of target cells. The entire trapped cell sample can be accurately analyzed without the need for any cell-specific labels. Key to the function of such a system is a label-free separation approach that has purity of represented by as a percentage by the formula (100*target cells/ (target cells+non-target cells)) above 30-50%, such that variations in cell capture of non-target blood cells do not overwhelm the specific signal from the target cells. These isolated cells can be analyzed to extract valuable data that may improve clinical decision-making. That is, the total count of large cells or distribution of cell size is used to help define a clinical decision concerning drug effectiveness, cancer relapse, initial cancer diagnosis, etc.

As described in the context of the embodiment of FIG. 1A, cells can be imaged in a smaller field of view when they are released from the vortices contained within the expansion regions 28 and flow downstream to the outlet 26. The width of the channel that is used as the outlet 26 flowing out of the device can be tuned to some extent but should normally be kept above ~800 μm to prevent increase in fluidic resistance and potential clogging at this choke point from all of the parallel channels. This outlet channel 26 can be imaged as explained herein. Compared to cells 48 within the vortices of the expansion regions 28, cells 48 in the outlet channel 26 are continuously flowing through the system, but at a lower velocity (0.2 m/sec) observed during the release, so continuous imaging at around 500 fps and 1 ms exposure time is sufficient to capture every cell 48 moving through the region and with <1 micron motion blur. The frame rate can be increased to 5000 fps and the width of the imaging area decreased to enable multiple measurements per cell 48 while maintaining the same camera specifications. Commercially mass-produced cameras and sensors can achieve these specifications.

As explained in the embodiment of FIG. 1D, cells 48 may be imaged while the same are in the vortices created within the expansion regions 28. The vortex trapping process has a final buffer wash step in which any residual RBCs and WBCs that are unstable within vortices or within low flow regions of the microchannel are washed out. This may take several seconds or up to a minute (e.g., between 10 seconds and 1 minute). Only large cells 48 remain trapped within the vortices and can then be imaged. Imaging requires a large field of view, since the chip that operates at 4 mL/min has 64 individual vortex traps that cover about 2 cm². Such a field of view (up to for example 18 cm²) can be analyzed using appropriately sized lenses to and magnification (either optical or digital) to cover the required field of view. Image frames or movies are captured as previously explained and individual cells within the captured frames are identified and analyzed with image processing software.

In another alternative embodiment, the cells 48 may be imaged after release from the purification device 12. Following the release step, captured cells 48 are collected "off-chip" in a concentrated suspension with a volume of around 300 μL. This volume fits in a single well in an SBS standard 96-well plate (has a FOV of approximately 40 mm²) which provides a fit to imaging using CCDs in a lens-free format. Cells 48 can also be released in a side chamber located on chip for potential static imaging and analysis, and released outside of the chip afterwards for potential downstream applications. Such processes would be enabled by the integration of valves into the device.

While imaging has been described largely using optical lenses and cameras or other CCDs, other approaches are possible. For example, there exist lens-free imaging solutions that can be used to image large fields of view with good resolution. These include lens-less holographic based imaging systems that are able to image small objects such as cells. For example, International Patent Publication No. 2011/049965 and U.S. Patent Application Publication No. 2012/0218329 disclose lens-free systems that have a large field-of-view that is capable of imaging and counting cells or particles.

An important aspect of this invention is that it is compatible with other applications downstream. This method of label-free analysis does not alter the collection of these cells for further downstream use of the cells, such as molecular characterization, cell growth, or label-based imaging. This invention can be used for other targets and other applications as well, such as the detection and analysis of Circulating Endothelial Cells as an early marker of coronary artery disease or for the trapping and analysis of rare stem cells from bodily fluids. While the invention finds particular utility with CTCs other cells can also be trapped and analyzed.

While emphasis has been made that the method and device can be used for the label-free analysis of cells, in some instances it may be beneficial to stain the cells before analysis in the system described herein. For example, cells can be stained with colorimetric nuclear stains before isolation within the vortices created within the expansion regions 28 to help the imaging process and provide more information. With discernable nuclear detail, nuclear size and nuclear-to-cytoplasmic ratio can be measured, which are standard cytological parameters that are then analyzed to make clinical diagnoses.

As described herein, cells passing through the microfluidic purification device 12 may be recirculated or re-injected back into the microfluidic purification device 12. For example, the outlet 26 of the purification device 12 may be coupled to a valve 32 than can be actuated to return concentrated cells back into the system 10 to trap more cells. This may be useful when particularly pure fractions are needed or required. Multiple passes through the purification device 12 may increase the purity of the collected cells 48.

While embodiments have been shown and described, various modifications may be made without departing from the scope of the inventive concepts disclosed herein. The invention(s), therefore, should not be limited, except to the following claims, and their equivalents.

What is claimed is:

1. A system for the label-free analysis of cells comprising:
    an adjustable flow rate pumping device coupled to a fluid sample containing a heterogeneous population of label-free cells;
    a purification device configured to receive the heterogeneous population of label-free cells, the purification device comprising an inlet coupled to the pumping device and further coupled to a plurality of microfluidic channels, each microfluidic channel having along a length thereof a plurality of expansion regions, and an outlet located downstream of the plurality of expansion regions, wherein vortices are generated in the expansion regions and temporarily trap therein a subpopulation of cells from the heterogeneous population of label-free cells in response to flow of the fluid sample within the microfluidic channels at a first flow rate from the adjustable flow rate pumping device and wherein the subpopulation of cells are released from the plurality of expansion regions and flow into the outlet at a second, reduced flow rate from the adjustable flow rate pumping device; and a high-speed camera imaging system positioned at an imaging region in the outlet and configured to acquire video images of the subpopulation of cells moving through the imaging region and comprising one or more processors executing image processing software configured to extract and process image frames in the video images and further configured to perform at least one assessment on the cells of the subpopulation comprising: count cells, measure cell size, and/or measure cell morphology.

2. The system of claim 1, wherein the subpopulation of cells comprises cancer cells.

3. The system of claim 1, wherein the expansion regions have a width between the range 400 μm and 600 μm and length within the range of 600 μm and 800 μm.

4. The system of claim 1, wherein the outlet is selectively coupled to the pumping device via a valve, wherein the pumping device is configured to recirculate the cells of the subpopulation back into the inlet.

5. A method for the label-free analysis of cells comprising:

flowing a heterogeneous population of label-free cells within a microfluidic device at a first flow rate, the microfluidic device comprising an inlet coupled to a pumping device and further coupled to a plurality of microfluidic channels, each microfluidic channel having along a length thereof a plurality of expansion regions;

trapping within vortices created in the plurality of expansion regions a subpopulation of cells from the heterogeneous population of label-free cells in response to flow of the fluid sample within the microfluidic channels;

reducing the flow rate through the microfluidic device to release the trapped subpopulation of cells from the plurality of expansion regions into an outlet; and capturing video images of the moving subpopulation of cells in the outlet with a high-speed camera;

subjecting the captured video images to image processing to isolate individual cells of the subpopulation;

automatically performing at least one of counting the trapped subpopulation of cells, measuring size of the trapped subpopulation of cells, and measuring morphology of the trapped subpopulation of cells.

6. The method of claim 5, wherein the subpopulation of cells comprises cancer cells.

7. The method of claim 5, wherein the heterogeneous population of label-free cells is contained within a bodily fluid selected from the group of blood, urine, pleural fluid, and peritoneal fluid.

8. The method of claim 5, wherein the subpopulation of cells trapped in the vortices comprises those cells having a size above a cutoff threshold size.

9. The method of claim 5, wherein cell morphology comprises cell circularity.

10. The method of claim 5, further comprising recirculating the trapped subpopulation of cells back into the inlet of the microfluidic device.

11. A method of characterizing the health of a subject from a fluid sample comprising:

flowing the fluid sample containing a heterogeneous population of label-free cells within a microfluidic device at a first flow rate, the microfluidic device comprising an outlet, an inlet coupled to a pumping device and further fluidically coupled to a plurality of microfluidic channels, each microfluidic channel having along a length thereof a plurality of expansion regions;

trapping within vortices created in the plurality of expansion regions a subpopulation of cells from the heterogeneous population of label-free cells in response to flow of the fluid sample within the microfluidic channels at the first flow rate;

reducing the flow rate through the microfluidic device to release the trapped subpopulation of cells from the plurality of expansion regions;

capturing video images of the moving subpopulation of cells in the outlet with a high-speed camera;

subjecting the captured video images to image processing to isolate and count individual cells of the subpopulation; and generating a characterization of the health of the subject based at least in part on the count of the subpopulation of cells, wherein the health of the subject is characterized as unhealthy when the count exceeds a threshold value.

12. The method of claim 11, wherein image processing further comprises identifying the size of each cell of the subpopulation and the characterization is based at least in part on the cell count and cell size.

13. The method of claim 11, wherein image processing further comprises measuring a morphological parameter including one or more of cell circularity, cell aspect ratio, cellular granularity, blebbing, membrane roughness, nuclear shape of the released subpopulation and basing the characterization at least in part on the morphological parameter.

14. The method of claim 11, wherein the unhealthy characterization comprises a cancer diagnosis.

15. The system of claim 1, wherein the outlet has a width of 800 μm.

16. The system of claim 1, wherein the high-speed camera acquires image frames a rate between about 500 to about 5,000 frames per second (fps).

17. The method of claim 5, wherein the moving subpopulation of cells move at a speed within the range of 0.1 to 0.4 m/s within the outlet.

* * * * *